US006786927B2

(12) United States Patent
Pallikaris et al.

(10) Patent No.: US 6,786,927 B2
(45) Date of Patent: Sep. 7, 2004

(54) DEVICE AND METHOD FOR THE INCREASE OF OCULAR ELASTICITY AND PREVENTION OF MACULAR DEGENERATION

(76) Inventors: Ioannis Pallikaris, Kalessa, Gazi of Heraklion (GR); Miltiadis K. Tsllibaris, 12, Magnisias Str, 71305 Heraklion Crete (GR); George A. Kounis, 8A, Efporon Str, Estravromenos 71407 Crete (GR); George D. Kymionis, 4, A. Sikelianou Str, Rethymno 74100 Crete (GR); Ginis S. Harilaos, Anopoleos str. 28, 71202, Heraklion (GR)

( * ) Notice: Subject to any disclaimer, the term of this patent is extended or adjusted under 35 U.S.C. 154(b) by 0 days.

(21) Appl. No.: 09/938,051

(22) Filed: Aug. 22, 2001

(65) Prior Publication Data
US 2002/0026240 A1 Feb. 28, 2002

(30) Foreign Application Priority Data
Aug. 24, 2000 (GR) ..................... 20000100291

(51) Int. Cl.[7] ............................. A61F 2/16; A61F 9/007
(52) U.S. Cl. ..................... 623/6.13; 623/6.41; 623/907
(58) Field of Search ............................. 623/6.13, 6.11, 623/6.22, 6.38–6.55, 4.1, 905, 907, 912; 604/521; 600/398

(56) References Cited

U.S. PATENT DOCUMENTS

| | | | |
|---|---|---|---|
| 4,588,406 A | * 5/1986 | Fedorov et al. ............ 623/6.38 |
| 4,883,485 A | * 11/1989 | Patel ......................... 623/6.13 |
| 4,902,293 A | * 2/1990 | Feaster ...................... 623/6.13 |
| 4,932,966 A | * 6/1990 | Christie et al. ............ 623/6.13 |
| 5,279,611 A | 1/1994 | McDonnell et al. | |
| 5,492,135 A | 2/1996 | DeVore et al. | |
| 5,807,381 A | 9/1998 | Lieberman | |

FOREIGN PATENT DOCUMENTS

| | | | |
|---|---|---|---|
| JP | 4-132547 A | * 5/1992 | ............. A61F/2/16 |
| WO | WO 92/17132 | * 10/1992 | ............. A61F/2/16 |

OTHER PUBLICATIONS

Ioannis G. Pallikaris, MD, Maria E. Papatzanaki, MD, Evdoxia Z. Stathi, MD, Oliver Frenschock, and Anthimos Georgiadis, PhD, *Laser in Situ Keratomileusis*, Lasers in Surgery and Medicine, vol. 10 pp. 463–468, 1990.

Stephen L. Trokel, M.D., R. Srinivasan, PhD., and Bodil Baren, B.A. *Excimer Laser Surgery of the Cornea*, vol. 96, No. 6, pp. 710–715, 1983, American Journal of Ophthalmology.

David S. Gartry, FRCS, FCOphth, Malcolm G. Kerr Muir, FRCS, FCOphth, John Marshall, PhD., *Photorefractive Keratectomy with an Argon Fluoride Excimer Laser: A Clinical Study*, vol. 7, pp. 420–435, Nov./Dec. 1991, Refractive & Corneal Surgery.

Terry J. Van Der Werff, D.Phil., *A New Single–Parameter Ocular Rigidity Function*, vol. 92, pp. 391–395 (1981), American Journal of Ophthalmology.

(List continued on next page.)

*Primary Examiner*—David H. Willse
(74) *Attorney, Agent, or Firm*—Brinks Hofer Gilson & Lione

(57) ABSTRACT

There is provided a compressible implant for the increase of ocular elasticity and the prevention of macular degeneration. This implantable intraocular device, which can be used for the prevention of ocular degeneration and especially of the macular degeneration through increase of total ocular elasticity. The device may be implanted either inside the ocular cavity or in contact with the eyeball.

14 Claims, 2 Drawing Sheets-

OTHER PUBLICATIONS

Winston Roberts M.D., and J. William Rogers, M.D., *Postural Effects on Pressure and Ocular Rigidity Measurements*, pp. 111–118. (Assumed published prior to filing date).

Peter P. Purslow, PhD, Wojciech S.S. Karwatowski, FRCOphth, *Ocular Elasticity*, pp. 1686–1692 (1996)., Ophthalmology, vol. 103, No. 10, Oct. 1996.

Joseph N. Simone, MD and Marc M. Whiteacre, MD, *The Effect of Intraocular Gas and Fluid Volumes on Intraocular Pressure*, Ophthalmology, vol. 97, No. 2, pp. 238–243 (1990), Ophthalmology, vol. 97, No. 2, Feb. 1990.

John E. Eisenlohr, M.E. Langham and A.E. Maumenee, *Manometric Studies of the Pressure–Volume Relationship in Living and Enucleated Eyes of Individual Human Subjects*, Brit. J. Ophthal., vol. 46, pp. 536–548 (1962).

Richard F. Brubaker, *Tonometry*, Clinical Ophthalmology, vol. 3, Chap. 47, pp. 1–7 (Assumed to be published before filing date).

Jonas S. Friedendwald, M.D., *Tonometer Calibration*, pp. 108–123 (1957), Trans Amer. Acad. of O & O, Jan.–Feb. 1957.

Carsten Edmund, *Corneal Elasticity and Ocular Rigidity in Normal and Keratoconic Eyes*, Acta Ophthalmologica, vol. 66, pp. 134–140 (1988).

Ephraim Friedman, MD, Sara Krupsky, MD, Anne Marie Lane, MPH, Setsuko S. Oak, Eric S. Friedman, MD, Kathleen Egan, MPH, Evangelos S. Gragoudas, MD, *Ocular Blood Flow Velocity in Age–Related Macular Degeneration*, Ophthalmology, vol. 102, No. 4, pp. 640–646 (1995).

Mark W, Johnson, MD, Dennis P. Han, MD, Kenneth E. Hoffman, MS, *The Effect of Scleral Buckling on Ocular Rigidity*, Ophthalmology, vol. 97, pp. 190–195 (1990).

Evangelos S. Gragoudas, MD, Suresh R. Chandra, MD, Ephraim Friedman, MD, Michael L. Klein, MD, Micael Van Buskirk, MD, *Disciform Degeneration of the Macula*, Arch Ophthalmol, vol. 94, pp. 755–757 (1976).

Ephraim Freidman, MD, *A Hemodynamic Model of the Phatogenesis of Age Related Macular Degeneration*, pp. 1–14 (1997), Am J. Opthalmol, Nov. 1997, 124 (5).

\* cited by examiner

DEVICE AND METHOD FOR THE INCREASE OF OCULAR ELASTICITY AND PREVENTION OF MACULAR DEGENERATION

BACKGROUND OF THE INVENTION

The decrease of the eye elasticity according to the rigid sclera theory, that was first stated by Friedman, in the previous decade, has a pathogenenetic role in the development of the age related macular degeneration. According to this theory the decrease of the elasticity of the sclera leads to increase of blood flow resistance inside choroid vessels and in a decrease of the filtration pressure in vessels walls. The sequence of these phenomena leads in defective transfer of fluid and metabolites from the retina to the choroid through the pigment epithelium. These useless metabolism products are accumulated in the Bruch's membrane, which is theorized to be the beginning of physiological and histological changes, which results in the macular degeneration, and the loss of optical acuity. This pathogenetic model is described in detail in the following publications:

Friedman E. Scleral rigidity, venous obstruction and age-related macular degeneration A working hypothesis. In: Ocular Circulation and Neovascularization. (Doc Ophthalmol Proc Ser) Ben Ezra D, Ryan S J and Murphy (eds). Dordrecht: NijhofVJunk Publishers 1987;50:197–204 35);

Fredman E. A hemodynamic model of the pathogenesis of age-related macular degeneration. Am J Ophthalmol 1977; 124(5):677–82 and Friedman E, Krupsky S, and Lane A et.al: Ocular blood flow velocity and age-related macular degeneration. Ophthalmol 195 5; 102:640–46

The apparent elasticity of the eyeball for every value of the intraocular pressure can be defined as the inverse gradients of the Intraocular Pressure vs. Eye Volume curve of any given eye. The methodology for the measurement of the apparent elasticity of the eyeball comprises controlled intraocular injection of non-compressible liquid and simultaneous measurement of the intraocular pressure. There are several techniques, which are described in various publications. Indicative references include the following:

Friedenwald J S. Contribution to the theory and practice of tonometry. Am J Ophthalmol 1937;20:985–1024

Van der Werff T J, Phil D. A new single-parameter ocular rigidity function. Am J Ophthalmol 1981;92:391395

In these publications the graphic representations and the mathematical description of the pressure dependence from the injected liquid volume inside the eyeball are presented. One accepted representation of this mathematical expression is the McEwen & St. Helens expression, which can be applied in some other mammal's eyes as well as to human eyes.

In the face of the hemodynamic model of Friedman and the pathogenic role which this model retains for the increased rigidity of the eye, several surgical techniques have been proposed, which aim to the increase the elasticity of the eyeball by increasing the elasticity of the sclera. For this purpose the sclera is made thinner by application of surface sclerectomies. Thus, the elasticity of the eyeball represents a parameter with clinical interest and it is desirable to be kept stable or be increased as a means for the prevention of the age related macular degeneration, especially in predisposed eyes.

For example, such a predisposition seems to exist in hyperopic eyes, which are also characterized by a relative increase of their thickness, as described in this recent publication:

Chaine G, Hullo A, Sabel J και συν:.Case-control study of the risk factors for the age related macular degeneration. France-DLMA Study Group. Br.J.Ophthalmol. 1998;82(9):996–1002

This combination of increased thickness along with decreased size makes hyperopic eyes appear less elastic (more rigid) than normal eyes.

SUMMARY

There is provided a compressible implant for the increase of ocular elasticity and the prevention of macular degeneration. This implantable intraocular device can be used for the prevention of ocular degeneration and especially of the macular degeneration through increase of total ocular elasticity. The device may be implanted either inside the ocular cavity or in contact with the eyeball. Other applications for the device may also include by way of example the improvement of the hemodynamic status of the eye in any situation associated with insufficient blood inflow. Situations of this kind other than AMD include: diabetic retinopathy, retinal vein thrombosis, retina artery obstruction, and glaucoma.

There is also provided a device implantable either in the eyeball or in the wall of the eyeball, serving for the increase of ocular elasticity where said device is characterized by that it is compressible either as a whole or parts of it. This device may further comprise the required optical elements, which can optically substitute the crystalline lens of the eye. Such a device may further comprise external dimensions and shape similar to the dimensions and shape of the crystalline lens, said device serving for the preservation of the volumetric relationship of the eye in the case that the crystalline lens has been removed. Such a device may yet further comprise a toroid capsule of external diameter about 8 mm to about 16 mm approximately, and internal diameter about 5 mm to about 12 mm, where said capsule is made of elastic or flexible membrane and contains gas or other compressible material. These devices may also comprise a capsule where said capsule is made of elastic or flexible membrane and contains gas or other compressible material and said device additionally features all the necessary optical elements for the optical substitution of the crystalline lens. These devices may also comprise a circular capsule, where said capsule is made of elastic or flexible membrane and contains gas or other compressible material, where said device has or may accept in its center, appropriate optical elements for the substitution of the normal eye lens. These device may also feature a capsule containing gas or other compressible material, said device additionally featuring optical elements where the refractive power of said elements can be controlled through addition or removal of gas or other compressible material from the capsule. In this materialization, appropriate manipulation of the refractive power of the compressible optical element (e.g. by the action of the ciliary muscle) can be used as a means of correction of presbyopia.

There is also provided a device that is capable of being implanted in the eye comprising: a toroid flexible sack, the flexible sack having an elastic side wall, the flexible sack being filled with a compressible material. The compressible material is used to maximize the volume of the flexible sack that can loose its shape to the internal pressure of the eye. The flexible sack contains a quantity of gas or other compressible material to occupy the flexible sack's maximum volume at the pressure of the interior of the eye. The compressible material in the sack typically includes a pressure of from about 4 mm Hg. to about 40 mm Hg. to maintain the shape of the flexible sack within the eye. When the flexible sack is inflated to its maximum size, the pressure of the compressible material equals the intraocular pressure. The elastic side wall includes a biocompatible material. In these devices the compressible material may be a gas, a foam, a gas contained in a foam. Moreover, the flexible sack may have an external diameter form about 8 mm to about 16 mm. and may further have an internal diameter from about 5 mm to about 12 mm.

There is also provided a device capable of being implanted in the eye comprising: a toroid flexible sack, the flexible sack having an elastic side wall, the flexible sack being filled with a gas, the gas having a pressure of from about 4 mm Hg. to about 40 mm Hg., the gas being selected from the group consisting of air, Nitrogen, Neon, $SF_6$, $C_3F_8$ and $CO_2$, the elastic side wall comprising a biocompatible material, the flexible sack having an external diameter from about 8 mm to about 16 mm and an internal diameter from about 5 mm to about 12 mm; and a valve.

There is still further provided a device for implantation into the eye comprising: a flexible sack filled with a compressible material; the flexible sack having an anterior side that is intended to be positioned nearer the anterior surface of the eye and a posterior side that is intended to be positioned nearer the posterior surface of the eye; the flexible sack having an interior surface and an exterior surface; the exterior surface intended to be positioned adjacent the wall of an eye; the interior surface forming a hollow frustum whereby when the device is implanted into the eye the flexible sack will not substantially interfere with light entering the eye; the frustum having an anterior end and a posterior end corresponding to the anterior side and posterior side of the sack; and, the anterior end of the frustum having a smaller diameter than the posterior end of the frustum. In these devices the flexible sack may further have an external diameter greater than about 7 mm. and may still further have the anterior end of the frustum of the flexible sack having an internal diameter greater than about 5 mm.

It is yet further provided a device for implantation into the eye comprising: a hollow frustum shaped flexible sack filled with a compressible material, the compressible material comprising a gas being selected from the group consisting of air, Nitrogen, Neon, $SF_6$, $C_3F_8$ and $CO_2$; the sack having a gas pressure from about 4 mm Hg. to about 40 mm Hg.; a valve for adding the gas to the flexible sack; the flexible sack having an elastic side wall; the elastic side wall consisting essentially of a biocompatible material; the flexible sack having an anterior side that is intended to be positioned nearer the anterior surface of the eye and a posterior side that is intended to be positioned nearer the posterior surface of the eye; the elastic side wall of the flexible sack forming an interior surface and an exterior surface; the exterior surface intended to be positioned adjacent the wall of an eye; the interior surface forming a hollow frustum whereby when the device is implanted into the eye and the flexible sack is filled with the gas the flexible sack will not substantially interfere with light entering the eye; the frustum having an anterior end and a posterior end corresponding respectively to the anterior side and posterior side of the sack; and, the anterior end of the frustum having a smaller diameter than the posterior end of the frustum.

There is also provided a device comprising: an optical means for focusing light generally on the retina of an eye; a means for increasing the apparent ocular elasticity of an eye; and, the optical means being contained within the means for increasing the apparent ocular elasticity of the eye, as well as a device comprising: an optical means for focusing light generally on the retina of an eye; and, a means for increasing the apparent ocular elasticity of an eye and for centering the optical means in the eye, as well as a device comprising: an optical means for focusing light generally on the retina of an eye and a means for increasing the apparent ocular elasticity of an eye, and as well as a device comprising: a lens and a means for increasing the apparent ocular elasticity of an eye and for centering the lens in the eye.

There is still further provided a device comprising: an optical means for focusing light generally on the retina of an eye; a means for increasing the blood supply to an eye; and, the optical means being contained within the means for increasing blood supply, as well as a device comprising: an optical means for focusing light generally on the retina of an eye; and, a means for increasing blood supply to the eye and for centering the optical means in the eye, as well as, a device comprising: a lens in an eye and a means for increasing blood supply to the eye, and as well as a device comprising: a lens and a means for increasing blood supply to an eye and for centering the lens in the eye.

There is still further provided an inflatable device for insertion into an eye comprising: a bag means for holding a compressible material, the bag means upon inflation with the compressible material having a donut shape; and, a valve means for permitting the addition of the compressible material to the bag means after the bag means has been inserted into an eye so as to inflate the bag in the eye.

There is still further provided a device capable of being implanted in the eye comprising: a donut shaped elastic bag, the elastic bag having a flexible side wall, the bag being capable of being filled with and holding a compressible material, the bag further being capable of maintaining a pressure once filled with the compressible material of from about 4 mm Hg. to about 40 mm Hg., and, the flexible side wall comprising a biocompatible material.

There is still further provided a device capable of being implanted in the eye comprising: a donut shaped elastic bag, the elastic bag having a flexible side wall and being filled with a compressible material, and, the compressible material exerting a pressure of from about 4 mm Hg. to about 40 mm Hg.

There is still further provided an optically implantable device comprising: a lens; a valve; a semi-flexible sack, the comprising a first elastic side wall, a second side wall, and a third side wall, the first, second and third side walls connected together to form the sack; the second side wall comprising a first relatively ridge optically significant face, and the side wall comprising a second relatively rigid optically significant face; and the lens being contained within the semi-flexible sack and located between the first and second optically significant faces.

There is also provided a method of increasing the apparent ocular elasticity of an eye comprising: inserting an inflatable device in the eye, the device comprising an elastic sack capable of being inflated with a compressible material; and inflating the device with a compressible material to between about 4 mm Hg. to about 40 mm Hg. pressure.

There is also provided a method of increasing the apparent ocular elasticity of an eye comprising: inserting a compressible elastic sack having a pressure of from about 4 mm Hg. to about 40 mm Hg.

DESCRIPTION

Figure 1:
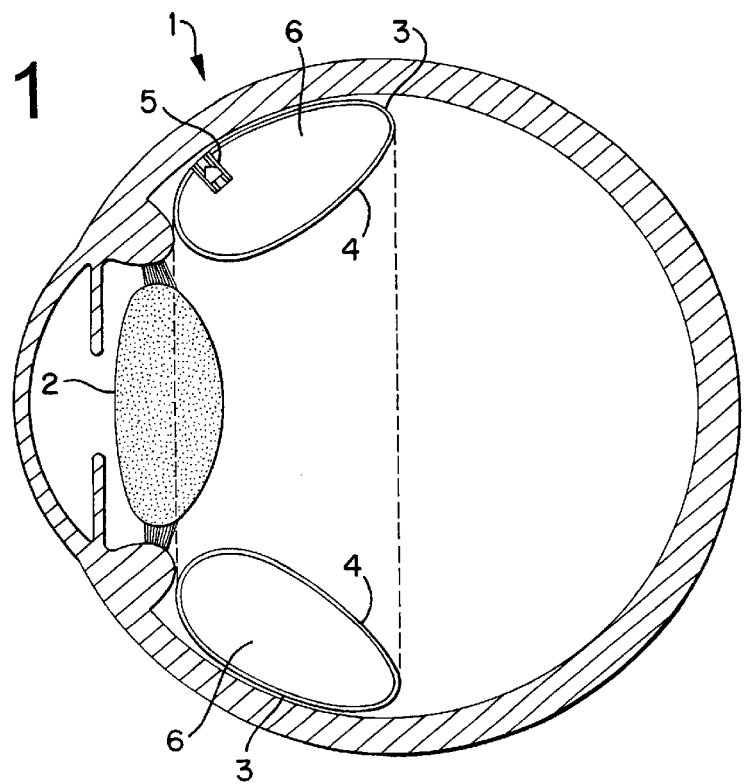
FIG. 1 is a cross section of an eye with a device implanted in the eye.

An analysis of the pressure-volume relation of the eye in basic engineering terms in order to describe the differential equation of pressure-volume relation (ocular rigidity) and to examine any possible correlation of rigidity and other parameters such as the presence of an intraocular air bubble, age of patients, axial length and pathologic eye conditions such as patients with age related macular degeneration (AMD) was studied. Ocular rigidity was determined in 50 eyes, operated for cataract, by injecting small increases of a balanced salt solution through the limbus in the anterior chamber, while continually monitoring the intraocular pressure with a transducer. A second measurement was obtained in all eyes after the injection of 0.05 ml air in the anterior chamber. Mean age was 65.8 years (range 42–86 years). 27 eyes had early AMD. Thus, the effective coefficient of scleral rigidity was not correlated with age of patients and axial length of the eye while there was a trend for increased rigidity in eyes with AMD. In parallel, air injection resulted in a slight downward displacement at the volume-pressure graph, indicating a decrease in ocular rigidity. Accordingly, it was concluded that this study provided an initial evaluation of the ocular rigidity in live human eyes. While ocular rigidity seems to be correlated with several parameters, such as age and axial length, there is evidence that ocular rigidity has some correlation with the presence of early stages of AMD. In addition, it was proved that intraocular air injection can decrease ocular rigidity.

An analysis of the effect of the presence of an intraocular gas bubble on ocular pulsation was studied. Corneal pulsation was evaluated by means of Goldman tonometry in 16 patients who received an intraocular gas injection in one eye as part of retinal detachment surgery. During the postoperative follow-up the gas fill was recorded as a percentage of vitreous cavity occupation, while corneal pulsation was evaluated at every visit. All patients presented corneal pulsation in both eyes preoperatively. In all patients no pulsation could be detected in the operated eye as long as the gas bubble occupied more than about 15% of the vitreous cavity volume. Pulsation gradually returned as the bubble volume diminished. When the bubble volume reached about 5% of the vitreous cavity volume, ocular pulsation became equal to that of the non-operated eye. Accordingly, it was concluded that the presence of an intraocular gas bubble can attenuate ocular pulsatility. Since ocular pulsation is related to ocular blood inflow, this observation may have clinical implications related to ocular blood supply.

There is provided a compressible implant for the increase of ocular elasticity and the prevention of macular degeneration. This implantable intraocular device, can be used for the prevention of ocular degeneration and especially of the macular degeneration through increase of total ocular elasticity. The device may be implanted either inside the ocular cavity or in contact with the eyeball. In case the device is implanted after removal of crystalline lens (in cataract surgery), besides the increase of elasticity, the device may protect the eye through the preservation of the volumetric relationship between its anatomical elements. The device may consist of a compressible material (e.g. foamed material), or from a sack filled with gas or other compressible material. In case the device is placed along the optical axis of the eye, besides the compressible part it should also comprise the necessary optical elements in order to function optically as a crystalline lens substitute. Thus, for example, and without limitation the device may be made from silicone, polyethylene, Poly—vinyl chloride (PVC), poly—methyl methacrylate (PMMA) or any other polymer that has both the desired mechanical properties and is biocompatible.

The device(s) can have several configurations, adaptations and applications, as show by way of illustration and without limitation in FIGS. 1–4. FIG. 1 shows a toroid sack that has been filled with gas after being implanted in the eye. In FIG. 1 there is shown a eye 1 having a crystalline lens 2 and a toroid sack 3 implanted within the eye. The sack 3 comprises an elastic or flexible wall 4 and a valve 5, which is used for filling the sack with a compressible material 6, e.g., gas such as air after implantation. There is provided a compressible implant for the increase of ocular elasticity, which may also be used for the treatment and the prevention of macular degeneration. This implantable device can be used for the increase of ocular elasticity.

Figure 2:
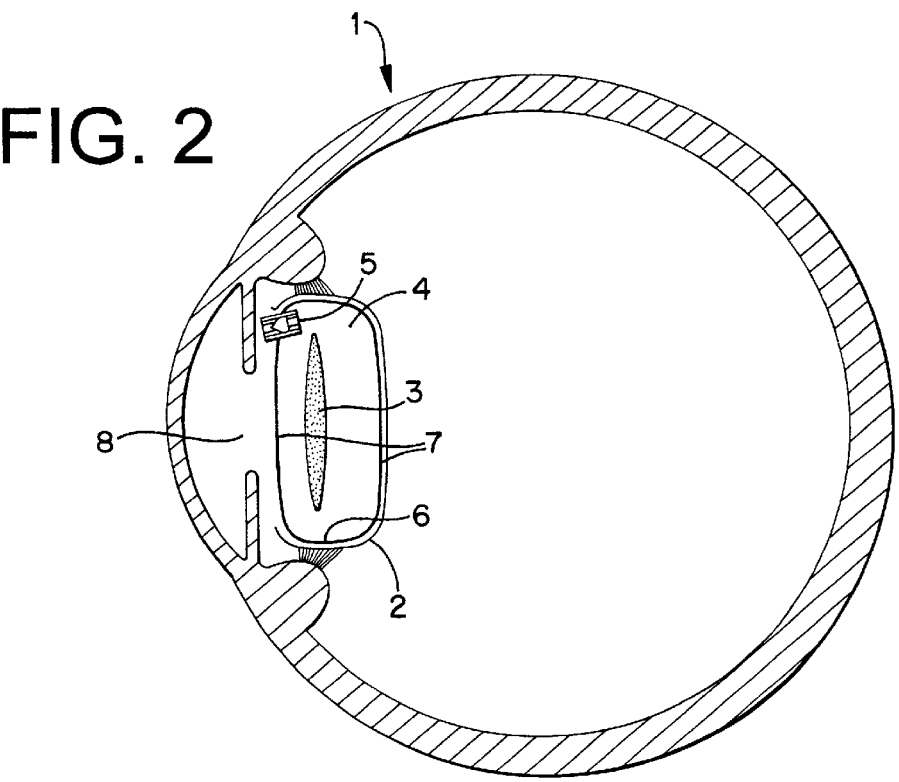
FIG. 2 is a cross section of an eye with a device implanted in the eye after cataract removal.

FIG. 2 shows a lens mount configuration of a device. In FIG. 2 there is shown an eye 1 having a device 8 implanted in the crystalline lens capsule 2 after cataract removal. The device 8 has a centrally mounted lens 3. The device 8 further comprises a sack 4 having a valve 5. The sack is capable of being filled with a compressible material, such as a gas, and in this Figure is shown as filled. The sack 4 has its outer sides 6 made from elastic or flexible material and axial faces 7 made from relatively rigid material having a predetermined (almost flat) shape. The optically significant axial faces have a rather consistent shape as shown by way of example in FIG. 2. Such a device as shown by way of example in FIG. 2 can increase ocular elasticity, and at the same time substitute the crystalline lens both optically and geometrically. The device's front and rear faces can be made relatively thick and mechanically stiff while the sides can be relatively elastic or flexible. Front and rear faces in that case could be made of some transparent polymer such as PMMA. Since the interior of the device will contain a gas (whose index of refraction is practically equal to 1), strong refraction will occur at the air-sack interface. For this reason the faces should be designed relatively flat to avoid excessive refraction. However, careful design of faces having the shape of a low power biconvex lens could introduce negative spherical aberration to compensate for the internal lens's positive spherical aberration and coma. Adding or removing material from the interior of such a device will accordingly vary its axial length (distance of one face from the other) and thus change its dioptric power. Thus, its optical power may be manipulated in order to achieve optimal focus for each given eye.

Figure 3:
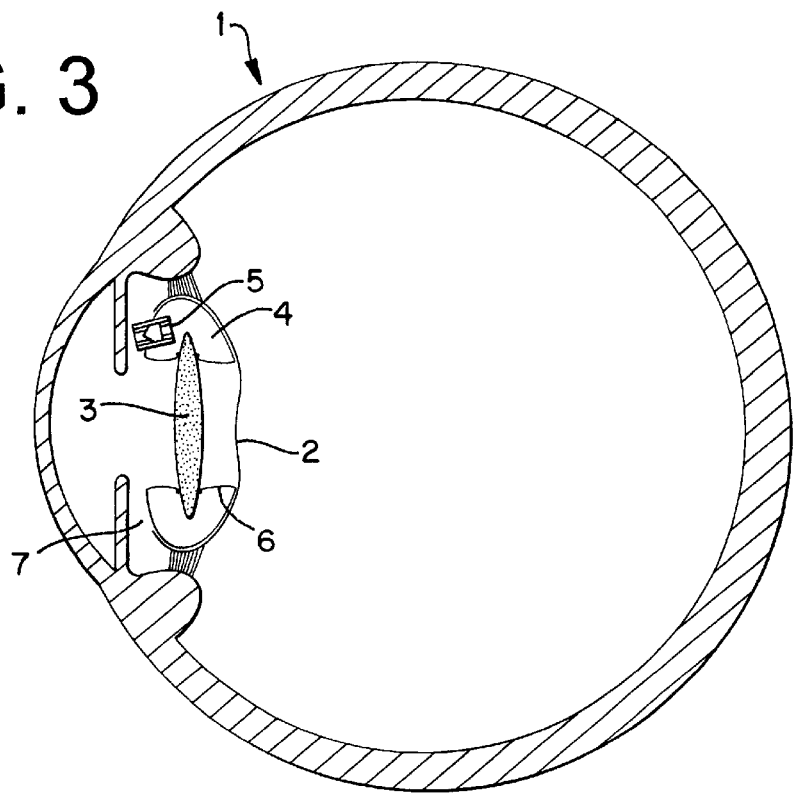
FIG. 3 is a cross section of an eye with another device implanted in the eye after cataract removal.

FIG. 3 shows another lens mount configuration of a device that has been implanted in the eye after removal of the crystalline lens, for example after cataract surgery. In FIG. 3 there is shown an eye 1 having a device 7 implanted in the crystalline lens capsule 2. The device 7 comprises a flexible air filled sack 4, a lens 3 and a valve 5. The sack 4 further comprises flexible or elastic side walls 6. The device as shown by way of illustration in FIG. 3 can feature an optical element (e.g., lens 3) that is mounted centrally within a compressible part (e.g., the sack 4) that surrounds the periphery of the optical element. In this way when the compressible part serves both for optical element centration and increase of ocular elasticity through its compressible nature.

Figure 4:
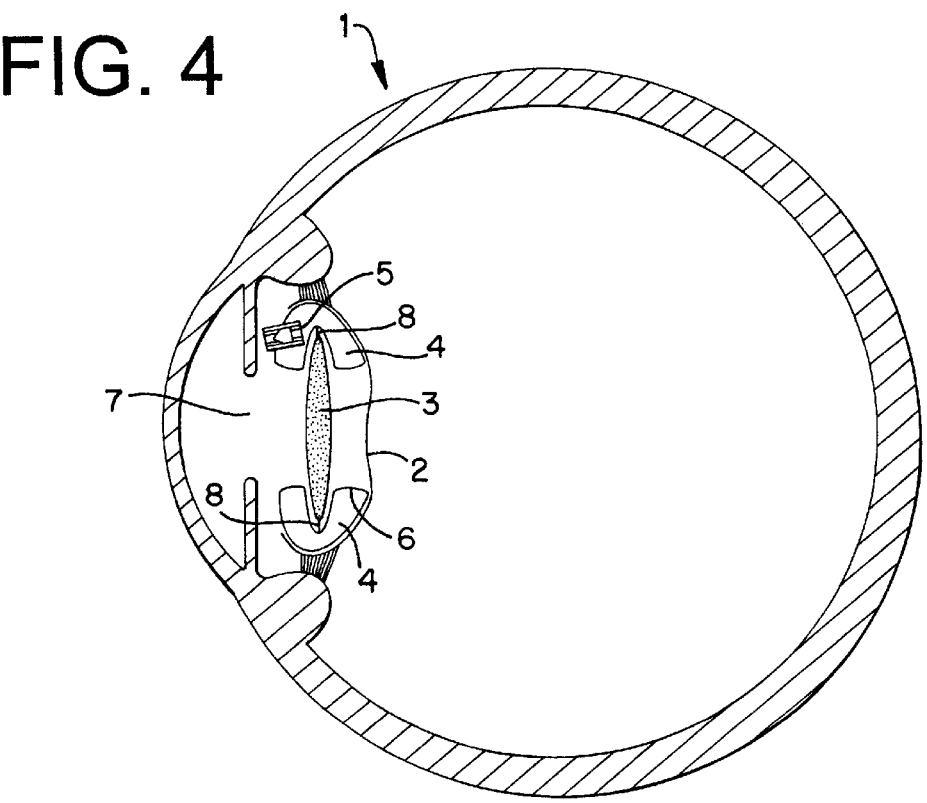
FIG. 4 is a cross section of an eye with another device implanted in the eye after cataract removal.

FIG. 4 shows a device that does not have an optical element but is adapted for use with a conventional intraocular lens with haptics. In FIG. 4 there is shown an eye 1 having a device 7 implanted in the lens capsule 2. The device 7 comprises a flexible sack 4, which is capable of being filled with a compressible material, such as a gas. In this Figure the device is shown as having already been filled with the gas. The device 7 further comprises a flexible side wall 6 and a valve 5. The device 7 is capable of being used with a conventional intraocular lens 3 with haptics 8.

There is provided a compressible implant for the increase of ocular elasticity, which may also be used for the treatment and the prevention of macular degeneration. This implantable device can be used for the increase of ocular elasticity. Thus, in a series of patients with intraocular gas after vitrectomies there has been shown to be a significant beneficial effect on ocular pulsatility, which is an indirect indication of significant hemodynamic effect of the intraocular gas. Additionally, the elasticity in a series of patients with and without intraocular air has been measured and from these measurements it has been documented that a significant increase of elasticity occurs after injection of air.

Thus, there is provided an intraocular implantable device, which is compressible and can increase the apparent ophthalmic elasticity. The increase of the elasticity is believed to be accomplished not by increasing the eye wall elasticity but through the compression of the device under the influence of the intraocular pressure. Although applicants are not bound by this theory of operation, and acknowledge that other manners of operation may be taking place in the device that give rise to the results that have been observed, it is believed that one can consider the choroid and retina vasculatur (which are the anatomic elements of interest) as the interior of a sandwich: the outer wall is the sclera which has some elasticity and the inner wall is the vitreous which is incompressible (no elasticity). If a compressible air-bag is added to the vitreous cavity then it is believed that there will be a change in this part from incompressible to compressible and thus there will be an increase in the overall elasticity of the eye. Thus, it is theorized that the air filled sack or air-bag provides more "space" to the vasculature to pulsate, permitting more blood to enter into the eye. Thus, one beneficial result that is being sought is an increase of ocular elasticity at any given intra-ocular pressure. If ocular elasticity is low (if the eye is very rigid) it accepts less blood with each heart pulse. This decreased ocular blood flow may be related to AMD. Prior attempts to achieve this elasticity increase have been made, focusing on the decrease of ocular wall rigidity (they made incisions etc.). The approach of the present device and method is to implant something compressible in the eye. (Blood entering the eye has to compress the implant instead of stretching the eye wall). Thus, the term apparent ocular elasticity is used because the eye itself is not affected; rather it appears to be more elastic from a haemodynamic point of view.

By way of illustration and without limitation it is desirable that the implantable device have some or all of the following basic characteristics.

a) It is constructed of biocompatible material, which should retain its elasticity as time passes.

b) It can be easily compressed with pressures ranging from several mmHg to several tens of mmHg, for example from about 40 mm to about 4 mm Hg, and more preferably from 20 mm Hg to 4 mm Hg. A compressible material is used to maximize the volume of the implantable device that can lose its shape to the internal pressure of the eye. When the implantable device is inflated to its maximum size, the pressure of the compressible material equals the intraocular pressure.

c) It is possible to be placed intaocularly.

d) It permits (either assists or does not impede) the formation of optical images on the retina.

e) In case the implantation is made simultaneously with a cataract extraction operation the device may, in addition to the elasticity attribute, offer the necessary elements for the optical and mechanical substitution of the normal lens.

In a preferable materialization of the invention, the implant consists of a sack, constructed by thin elastic silicone membrane, which is filled with compressible material (e.g., air or other gas). In another preferable materialization the sack construction material is flexible PVC or polyethylene membrane or polyethylene. In another materialization the material is foam material and includes in its bubbles the necessary space of compressible medium (e.g., gas). In order for the placement to be minimally invasive, the device may constructed so that it has, initially, small dimensions while the gas may be placed inside the implant, after the insertion into the eyeball, through a small hole.

Possible gases that may be used as compressible materials included by way of example and without limitation air, Nitrogen, Helium, Neon, $SF_6$, $C_3F_8$ and $CO_2$. All compressible materials, either foam or gases, are preferably biocompatible and clean (e.g. filtered) to avoid infection of the eye in case of leakage.

In another materialization the device comprises a toroid sack, which may be placed in the posterior chamber and filled with gas after its placement. In this case the device does not take part in the shaping of the image in the retina. The elastic membrane from which the sack is constructed may have suitable color and texture so that there are no light reflections in the eyeball interior.

In another materialization, the device may be constructed from transparent, elastic material and besides the prerequisite volume, may have optical elements for the substitution of the normal lens. Beyond the elastic encasement it is possible for the optical element to be elastic also, so that there is the possibility for the entire device to be folded properly and inserted in the eyeball through a small hole. In this case it is important to quantify the refractive role of the sack-gas interface. The curvature of those surfaces—and hence their refractive power—is possible to be defined from the quantity of the inserted gas. In this case it is possible to make micro adjustments of the implant refraction after its placement. In another preferable materialization the compressible part of the device does not get in the refraction but it consists of the haptic element of a typical intraocular lens. This gas insertion and the eventual expansion of this haptic may contribute in the better anatomic centralization and alignment of the intraocular lens.

The device after its implantation accepts the buoyancy of the aqueous medium in which it is dipped. In cases where the mean density of the device may be much less than that of the aqueous medium (like in the case in which the device comprises a sack full of gas), for its equilibrium in the interior of the eye a force opposite that of the net buoyancy will be necessary to be exerted. If deemed necessary this net buoyancy may possibly be minimized by the insertion of suitable weight on or in the implant.

The following examples are materializations of the invention and are provided as illustrative variations of the invention and in no way restrict or limit it.

EXAMPLE 1

One toroidal sack of external diameter about 16 mm and internal of about 9 mm is constructed from thin elastic biocompatible membrane. In some point of the periphery there is an intake valve from which a quantity of gas from 0.05 ml to 0.3 ml in 1 atm pressure may be inserted in the sack. The sack is initially empty and folded in such a way that it can be inserted in the posterior chamber from an opening of about 2 mm in the corneoscleral limbus, the cornea or the sclera. After the insertion of the sack into the eyeball, in the intake valve port it is possible to place a needle from which a predetermined quantity of air can be inserted. This air fill-in of the sack will lead to its expansion and its adaptation in the periphery of the eyeball. A suitable intake valve may comprise by way of example and without limitation simply using a fine needle to puncture the sack; the sack material having sufficient elasticity that it will seal itself when the needle is removed.

EXAMPLE 2

One toroidal sack of external diameter about 16 mm and internal of about 9 mm is constructed from thin elastic biocombatible membrane. The construction material is sufficiently elastic to allow its temporal punching with a thin needle, after the removal of which needle, the hole created, will close in such a way that the leak of the inserted gas will not be permitted. The sack is initially empty and folded in such a way that it can be inserted in the posterior chamber from an opening of 2 mm in the corneoscleral limbus, the cornea or the sclera. After the insertion of the sack in the eyeball, and the punching from the needle a predetermined quantity of air can be inserted. This air fill-in of the sack will lead to its expansion and its adaptation in the periphery of the eyeball.

EXAMPLE 3

A lenticular sack, which has in its center a coaxial, converging optical element is provided. This optical element is elastic so that if it deformed (e.g., bended or folded), it regains its normal shape when forces that keep it deformed are no longer applied to it. From material with the same properties are constructed also the parts of the sack which are perpendicular in the optical axis of the compound optical element, while the peripheral part of the sack may be constructed from the same or other flexible material. The optical element is placed in the periphery of the sack in such a way that allows the fill-in of both the two compartments from both sides of the optical elements from one point of gas insertion. In one point of the periphery there is an intake valve from which it is possible to insert to the sack quantity of gas from 0.05 ml to 0.3 ml in 1 atm pressure. The sack is initially empty and folded in such a way in which can be inserted in the lens capsule from which the normal lens has been extracted from a typical phacoemulsification incision. After the insertion of the sack in the eyeball a needle can be inserted to the intake valve port from which predetermined quantity of gas can be inserted. This air fill-in of the sack will lead to its expansion and adaptation in the periphery inside the lens capsule, and simultaneously folding and alignment of the sack's optical elements and refractive surfaces.

EXAMPLE 4

A sack of cordate shape by rotation around its axis which has fixed inside a converging optical element, is provided. The optical element is elastic so that if it is deformed (e.g., bended or folded) it can retrieve its normal shape when the deformation forces are no longer applied. In one point of the periphery there is an intake valve from which it is possible to insert into the sack quantity of gas from 0.05 ml to 0.3 ml in 1 atm pressure. The sack is initially empty and folded with the optical element in such a way that it can be inserted in the eye lens capsule from which the normal lens has been extracted using a typical phacoemulsification incision. After the insertion of the sack into the eyeball, it is possible to fit a needle in the intake valve port and a predetermined quantity of air can be inserted. This air fill-in of the sack will lead to its expansion and adaptation in the periphery inside the lens capsule, and simultaneously folding and alignment of the sack's optical elements.

EXAMPLE 5

A sack of cordate shape by rotation around its axis may accept in its center a typical intraocular lens. In one point of the periphery there is an intake valve from which it is possible to insert into the sack a quantity of gas from about 0.05 ml to 0.3 ml in 1 atm pressure (the pressure is maintained by removing the same volume of aqueous from the eye as gas added). The sack is initially empty and folded in such a way that it can be inserted in the eye lens capsule from which the normal lens has been extracted using a typical phacoemulsification incision. After the insertion of the sack in the eyeball, is possible to fit a needle in the intake valve and a predetermined quantity of air can be inserted. This air fill-in of the sack will lead to its expansion and adaptation in the periphery inside the lens capsule. Thereafter the optical element can be placed in the sack.

EXAMPLE 6

A sack of cordate shape by rotation around its axis which may accept in its center a typical intraocular lens is provided. The construction material is sufficiently elastic to allow its temporal punching with a thin needle, such that after the needle is removed, the hole created will close in a way that leaking of the inserted gas will not be permitted. The sack is initially empty and folded in such a way in which it can be inserted in the eye lens capsule from which the normal lens has been extracted using a typical phacoemulsification incision. After the insertion of the sack into the eyeball, and the punching from the needle, a predetermined quantity of air can be inserted. This air fill-in of the sack will lead to its expansion and adaptation in the periphery inside the lens capsule. Thereafter the optical element can be placed in the sack.

The foregoing detailed description has been provided by way of explanation and illustration, and is not intended to limit the scope of the appended claims. Many variations in the presently preferred embodiments illustrated herein will be obvious to one of ordinary skill in the art, and remain within the scope of the appended claims and their equivalents.

We claim:

1. A method of increasing the apparent ocular elasticity of an eye comprising:
    inserting an inflatable device in the eye, the device being of generally toroidal shape, the device having a generally U-shaped cross section with an inward-facing channel; and
    inflating the device with a compressible material.

2. The method of claim 1 wherein the compressible material comprises a gas.

3. The method of claim 1 wherein the compressible material comprises a foam.

4. The method of claim 1 further comprising the step of providing a weight on the device to regulate the buoyancy of the device.

5. The method of claim 1 further comprising positioning an optical lens within an inner diameter of the device, wherein the outer periphery of the lens is positioned within the channel in the device.

6. The method of claim 1, further comprising a valve connected to the device, wherein the compressible material is inserted through the valve.

7. A method of increasing the apparent ocular elasticity of an eye comprising:

measuring a first ocular rigidity of the eye;

inserting an inflatable device in the eye, the device being of generally toroidal shape and capable of being filled with a compressible material;

inflating the device with the compressible material; and measuring a second ocular rigidity of the eye.

8. The method of claim 7 wherein the second ocular rigidity is less than the first ocular rigidity.

9. The method of claim 7 wherein the compressible material comprises a gas.

10. The method of claim 7 wherein the compressible material comprises a foam.

11. The method of claim 7 further comprising the step of providing a weight on the device to regulate the buoyancy of the device.

12. The method of claim 7 wherein the device has a generally U-shaped cross section with an inward-facing channel.

13. The method of claim 12 further comprising the step of positioning an optical lens within an inner diameter of the device, wherein the outer periphery of the lens is positioned within the channel in the device.

14. The method of claim 7, wherein the device further comprises a valve, wherein the compressible material is inserted through the valve.

* * * * *